United States Patent [19]

Schapira et al.

[11] Patent Number: 5,695,773

[45] Date of Patent: Dec. 9, 1997

[54] PHYTOSANITARY COMPOSITION CONTAINING A COMBINATION OF AN OXYNIL AND AT LEAST ONE SUBSTANCE LIQUID AT AMBIENT TEMPERATURE AND A PROCESS FOR APPLYING THESE COMPOSITIONS

[75] Inventors: Joseph Schapira, Paris; Jacques Pecheur, Colombes; Dominique Ambrosi, Courbevoie, all of France

[73] Assignee: CFPI Agro, Gennevilliers, France

[21] Appl. No.: 353,337

[22] Filed: Dec. 5, 1994

Related U.S. Application Data

[63] Continuation of Ser. No. 2,399, Jan. 13, 1993, abandoned.

[30] Foreign Application Priority Data

Jan. 13, 1992 [FR] France ................... 9200267

[51] Int. Cl.⁶ .................... A01N 25/02; A01N 37/34
[52] U.S. Cl. .................... 424/405; 424/406; 514/741; 504/141
[58] Field of Search .................... 424/405, 406; 504/141; 514/741

[56] References Cited

FOREIGN PATENT DOCUMENTS

| | | |
|---|---|---|
| 0 031 684 | 7/1981 | European Pat. Off. . |
| 0031684 | 7/1981 | European Pat. Off. . |
| 0 064 478 | 11/1982 | European Pat. Off. . |
| 0 210 818 | 2/1987 | European Pat. Off. . |
| 3210818 | 2/1987 | European Pat. Off. . |
| 0 219 143 | 4/1987 | European Pat. Off. . |
| 0 228 943 | 7/1987 | European Pat. Off. . |
| 0 229 558 | 7/1987 | European Pat. Off. . |
| 0 432 061 | 6/1991 | European Pat. Off. . |
| 0432061 | 6/1991 | European Pat. Off. . |
| 2 556 933 | 6/1985 | France . |

OTHER PUBLICATIONS

Wilson et al., "The Effects of Two Phytobland Oils on the Postemergence...", Proc. Northeast Weed Contr. Conf, vol. 22, Jan. 1968, pp. 294–298.

Sarpe et al., "Efficacite Des Herbicides Bentazon, Bromoxynil–K/Mcpa . . . ", Compte Rendu 11eMe Confe'rence Columa, vol. 2, 1981, France, pp. 434–440.

Chemical Patents Index, Documentation Abstracts Journal, Section Ch, Week 9105, Apr. 1991, Derwent Publications, Ltd., London GB; Class C, AN 037005.

*Primary Examiner*—Neil S. Levy
*Attorney, Agent, or Firm*—Larson & Taylor

[57] ABSTRACT

A phytosanitary composition, characterized in that it contains a combination of an oxynil and at least one substance selected from the group consisting of herbicides, insecticides, fungicides, growth regulators and/or pesticides, this substance which is liquid at ambient temperature being intended to keep the oxynil in the liquid state at the application site, if necessary after it has been brought into the liquid state.

5 Claims, No Drawings

PHYTOSANITARY COMPOSITION CONTAINING A COMBINATION OF AN OXYNIL AND AT LEAST ONE SUBSTANCE LIQUID AT AMBIENT TEMPERATURE AND A PROCESS FOR APPLYING THESE COMPOSITIONS

This application is a continuation of application Ser. No. 08/002,399 filed Jan. 13, 1993, abandoned.

This invention relates to phytosanitary compositions of the type containing an oxynil and at least one substance liquid at ambient temperature.

The invention also relates to a process for applying these compositions.

In the context of the invention, the term "oxynil" is understood to apply generally to hydroxybenzonitriles, including 4-hydroxy-3,5-dibromobenzonitrile or bromoxynil ou and 4-hydroxy-3,5-diiodobenzonitrile or ioxynil, their salts and their esters.

Phytosanitary compositions containing oxynils as selective herbicides are already known.

It is also known that, in addition to the use of herbicides, the complete treatment of plants often requires the use of insecticides, fungicides, growth regulators or any other pesticide. In overall terms, this corresponds on the one hand to a very significant consumption of chemical products by the agriculturalist and hence to an increase in the retail price of cultivated plants, and also to an accumulation in the cultivated soils of those chemical products, which presents pollution and environmental problems, and on the other hand to a loss of time for agriculturalists who have to successively apply as many treatments as necessary to their plants.

Now, after extensive studies, Applicants have succeeded in developing preparations for the treatment of plants, which are less onerous and easier to use, in the form of a phytosanitary composition which is characterized in that it contains a combination of an oxynil and at least one substance selected from the group comprising insecticides, fungicides, growth regulators, pesticides and/or herbicides selected from the group comprising S-alkyl- and S-benzyl-thiolcarbamates, chloracetanides, and herbicides selected from the group consisting of butamifos, cinmethylin, clethodim, isopropalin, olomazone, dalepen, tebutame, sulfosate, methyl (R)-2(7-(2-chloro-α,α,α-trifluoro-p-tolyloxy)-2-naphthyloxy) propionate and (+)-tetrahydrofurfuryle (R)-2-[4-(6-chloro-quinoxaline-2-yloxy)phenoxy] propanoate, fluazifop-butyl and sethoxydime, this substance which is liquid at ambient temperature being intended to keep the oxynil in the liquid state at the application site, if necessary after it has been brought into the liquid state, with the proviso that, in cases where the substance is a herbicide consisting of an S-benzyl-thiolcarbamate selected from the group consisting of thiobencarbe, orbencarbe, thiocarbazil, prosulfocarbe and esprocarbe, the ratio of S-benzyl-thiolcarbamate to ioxynil is below 2.5, fluazifop-butyl or fluazifop-p-butyl, the ratio fluazifop-butyl to oxynil or fluazifop-p-butyl to oxynil is above 0.7, sethoxydime, the ratio sethoxydime to oxynil is below 0.4.

It has been found that, in the case of this phytosanitary composition containing a combination of an oxynil used in a dose in which, on its own, it shows little, if any, activity and at least one of the above-mentioned substances liquid at room temperature, a synergistic effect is surprisingly and unexpectedly developed between the oxynil and the substance liquid at ambient temperature.

In the context of the invention, a pesticide is understood to be any chemical product used in agriculture other than herbicides, insecticides, fungicides and growth regulators, such as for example a bactericide or a herbicide antidote.

In cases where the substance liquid at ambient temperature is a herbicide, not only is the herbicidal effect of the oxynil potentiated, it may even be completed by the activity of the other herbicide used as the substance liquid at ambient temperature. Accordingly, the spectrum of activity of the herbicidal composition according to the invention can be broadened and a complete herbicidal treatment of this type can thus be applied in a single step to the plant to be treated.

In cases where the substance liquid at ambient temperature combined with the oxynil is an insecticide, a fungicide, a growth regulator or any other pesticide, the herbicidal effect of the oxynil is always potentiated by the substance which may also have an effect of its own. Accordingly, phytosanitary compositions of this type perform a dual function on the plants to be treated: herbicide-insecticide, herbicide-fungicide, herbicide-growth regulator or herbicide-pesticide, depending on the substance liquid at ambient temperature which is combined with the oxynil. A single application of this type of composition enables the plant to be subjected to a double treatment at any time.

The combination with an oxynil of a mixture of at least two substances, of which at least one is liquid at ambient temperature, to obtain a phytosanitary composition according to the invention having at least a triple effect on the plants to be treated is also possible providing the substances used are chemically compatible with one another.

The expression "substance liquid at ambient temperature" is understood to mean that the substance has a melting point of or below 30° C.

The phytosanitary compositions according to the invention contain 48 to 450 g/l oxynil and may be formulated as:
concentrated suspensions,
emulsifiable concentrates,
aqueous emulsions,
true solutions,
oily emulsions.

In addition to the combination of an oxynil and at least one substance liquid at ambient temperature, the phytosanitary composition according to the invention may comprise one or more ionic or nonionic surfactants and a diluent.

The surfactants may be selected from the nonionic and anionic surfactants listed in the annual publication (North American Edition et International Edition) edited by McCutcheon's Division MC Publishing Company and relating to "Emulsifiers & Detergents" or in the index of surfactants published by B. Parant in D.T.A. (France).

The nonionic surfactants suitable for use in accordance with the invention are those obtainable by the condensation of one or more mols ethylene and/or propylene oxide with short-chain or fatty alcohols, alkylphenols, fatty amines, fatty amides, polystyrylphenols.

The anionic surfactants include alkylarylsulfonates in the form of alkali metal salts, alkaline earth metal salts or alkanolamines, soaps, phosphoric esters of the nonionic surfactants mentioned above, polynaphthylmethanepolysulfonates and their alkylated derivatives, lignosulfonates and polymers containing several carboxylic functions.

The diluent is selected from the group consisting of water, acetophenone, cyclohexanone, isophorone, toluene, xylene, dimethyl-sulfoxide (or DMSO). It is emphasized that, where they are liquid, the anionic or nonionic surfactants may also serve as diluents.

The phytosanitary composition according to the invention may also comprise such additives as protective agents, penetration agents, stabilizers, volatility reducing agents, sequestrants, colourants and corrosion inhibitors. It should be noted that, in certain cases, these additives may also serve as diluents.

The phytosanitary composition according to the invention may be prepared from a liquid concentrate using the diluents mentioned above.

It is of advantage to start from a self-emulsifiable concentrate containing a combination of an oxynil and at least one of the above-mentioned substances liquid at ambient temperature dissolved in an emulsifier or in a solvent. By preparing the phytosanitary composition from such a concentrate by addition of water, a ready-to-use liquid product according to the invention is obtained.

Finally, the invention also relates to the use of the ready-to-use sprays containing the active constituent(s) in the concentration required to obtain biological results.

The process for applying the phytosanitary compositions according to the invention is characterized in that the phytosanitary compositions are applied to the plant to be treated by spraying in a quantity sufficient to distribute 48 to 450 grams oxynil per hectare of treated plants.

The phytosanitary composition according to the invention may be applied to the soil by conventional techniques using, for example, hand pump sprayers, power sprayers or pre-pressurized sprayers equipped with application distributors or nozzles well known to the expert.

The products or groups of products from which the substances liquid at ambient temperature intended to keep the oxynil in the liquid state at the application site, if necessary after it has been brought into the liquid state, are selected and the dosages in which they are used for the application of the phytosanitary compositions according to the invention are described in the following; these products or groups of products are herbicides, insecticides, fungicides, growth regulators and pesticides.

The substances liquid at ambient temperature which form part of the composition according to the invention are designated hereinafter either by their chemical names or by their common names; in the latter case, the corresponding chemical names can be found in "The Pesticide Manual", Ninth Edition, published by The British Crop Protection Council.

The herbicides are selected from:

the S-benzyl-thiolcarbamates comprising thiobencarbe, orbencarbe, thiocarbazil, prosulfocarbe and esprocarbe used for the preparation of the phytosanitary compositions according to the invention in such a quantity that the ratio of herbicide to ioxynil is below 2.5, the S-alkyl-thiolcarbamates comprising EPTC, pebulate, cycloate, butylate, vernolate, diallate, triallate and molinate used for the preparation of the phytosanitary compositions according to the invention in a concentration of 200 a 970 g/l and used at the application site in quantities of 10 to 2000 g/ha and preferably in quantities of 50 to 1000 g/ha, the chloracetanilides comprising acetochlore, butachlore, butenachlore, metolachlore and pretilachlore used for the preparation of phytosanitary compositions according to the invention in a concentration of 200 to 970 g/l and used at the application site in quantities of 10 to 2000 g/ha and preferably in quantities of 50 to 1000 g/ha, butamifos, cinmethylin, clethodim, isopropalin, clomazone, dalapen, tebutame, sulfosate, methyl (R)-2(7-(2-chloro-α,α,α-trifluoro-p-tolyloxy)-2-naphthyloxy) propionate and (+)-tetrahydrofurfuryle (R)-1-[4-(6-chloro-quinoxaline-2-yloxy)phenoxy] propanoate used for the preparation of phytosanitary compositions according to the invention in a concentration of 40 to 800 g/l and used at the application site in quantities of 10 to 2000 g/ha and preferably in quantities of 50 to 1000 g/ha, fluazifop-butyl or fluazifop-p-butyl used for the preparation of phytosanitary compositions according to the invention in such a quantity that the ratio fluazifop-butyl to oxynil or fluazifop-p-butyl to oxynil is above 0.7 and used et the application site in quantities of 50 to 275 g/ha, sethoxydime used for the preparation of phytosanitary compositions according to the invention in such a quantity that the ratio of sethoxydime to oxynil is below 0.4 and used at the application site in a quantity of 50 to 275 g/ha.

The insecticides are selected from:

the pyrethrinoids comprising allethrine, resmethrine, cyhalothrine, cyphenothrine, permethrine, empenthrine, cycloprothrine, flucythrinate, fluvalinate, fenvalerate and their natural or synthetic isomers used for the preparation of the phytosanitary compositions according to the invention in a concentration of 1 to 500 g/l and used at the application site in quantities of 5 to 200 g/ha and preferably in quantities of 10 to 100 g/ha, organophosphorus compounds comprising cadusafos, chlorfenvinphos, cyanophos, demethon-S-methyl, diazinon, dichlorvos, dicrotophos, disulfoton, edifenphos, ethion, ethoprophos, etrimphos, fenitrothion, fensulfothion, fenthion, fonofos, formothion, heptenophos, isazofos, isofenphos, isoxathion, malathion, mecarbam, mephosfolan, naled, omethoate, oxydemeton-methyl, methacrifos, mevinphos, parathion, phenthoate, phorate, phosphamidon, phoxime, piperophos, pirimiphos, profenofos, propaphos, propetamphos, prothiofos, pyraclofos, sulfotep, sulprofos, terbufos, thiometon and triazophos in the form of their various esters, particularly methyl and ethyl esters, used for the preparation of the phytosanitary compositions according to the invention in a concentration of 10 to 1000 g/l and used at the application site in quantities of 10 to 1000 g/ha and preferably in quantities of 50 to 500 g/ha, benfuracarbe, carbosulfan, furathiocarbe and propargite, used for the preparation of the phytosanitary compositions according to the invention in a concentration of 100 to 800 g/l and used at the application site in quantities of 10 to 1000 g/ha and preferably in quantities of 50 to 500 g/ha.

The fungicides are selected from:

etridiazole, fenpropidine, fenpropimorphe, tridemorphe, iprobenfos, propiconazole, tetraconazole and pyrifenox, used for the preparation of the phytosanitary compositions according to the invention in a concentration of 50 to 750 g/l and used at the application site in quantities of 5 to 1000 g/ha and preferably in quantities of 10 to 750 g/ha, The growth regulators are selected from:

etacelasil, heptopargil and hydrazinoethanol used for the preparation of the phytosanitary compositions according to the invention in a concentration of 200 to 800 g/l and used at the application site in quantities of 10 to 2000 g/ha and preferably in quantities of 50 to 1000 g/ha.

The pesticides include:

methoprene, dimethylphthalate, diethyltoluamide and fluxofenim used for the preparation of the phytosanitary compositions according to the invention in a concentration of 40 to 1000 g/l and used at the application site in quantities of 10 to 1000 g/ha and preferably in quantities of 50 to 500 g/ha.

The following examples, which are intended to enable the invention to be better understood without limiting it in any way, are given purely by way of illustration in conjunction with advantageous embodiments.

EXAMPLE 1

Composition based on ioxynil octanoate and prosulfocarbe

A phytosanitary composition according to the invention was prepared in the form of an emulsifiable concentrate containing 192 g/l of ioxynil octanoate and
480 g/l of prosulfocarbe and was applied by spraying in a quantity of 0.5 l/ha to plants of *Chenopodium album*, *Galium aparine* and

*Veronica sp.* in pots, at the 3 to 4 leaf stage in the doses indicated in Table I.

The herbicidal effect of the composition on the treated species was evaluated after 21 days.

The results of this test are set out in Table I.

The expression "Expected Results" is used to denote the percentage destruction of the plants calculated by addition of the effect of oxynil applied on its own (x) on the one hand and the effect of the substance liquid at ambient temperature applied on its own (Y) on the other hand, taking into account their respective application doses, in accordance with the following formula:

$$X + Y = \frac{XY}{100},$$

where X and Y represent the percentages destruction of the treated plants observed in relation to an untreated control for which the destruction of the plants is considered as being 0%, the observation being made 21 days after the treatment.

The expression "Results obtained" is used to denote the percentage destruction of the treated plants obtained in relation to an untreated control for which the destruction of the plants is considered as being 0%.

There is a synergistic effect between the oxynil and the substance liquid at ambient temperature which are present in combination in the phytosanitary compositions according to the invention whenever the results obtained are better than the expected results.

TABLE I

|  | Results obtained (%) after individual application of the constituents of the composition | | Expected results (%) | Results obtained (%) |
|---|---|---|---|---|
| Ioxynil octanoate (g/ha) | 96 | 0 | 96 | 96 |
| Prosulfocarbe (g/ha) | 0 | 240 | 240 | 240 |
| Chenopodium album | 15 | 0 | 15 | 100 |
| Galium aparine | 35 | 10 | 42 | 55 |
| Veronica sp. | 50 | 0 | 50 | 75 |

It can be seen from this Table that a synergistic effect is developed between the ioxynil octanoate and the prosulfocarbe.

EXAMPLE 2

Composition based on bromoxynil octanoate and prosulfocarbe

Three phytosanitary compositions according to the invention were prepared in the form of emulsifiable concentrates of which the respective formulations are shown in Table II below:

TABLE II

|  | Bromoxynil octanoate (g/l) | Prosulfocarbe (g/l) |
|---|---|---|
| Composition 1 | 100 | 240 |
| Composition 2 | 200 | 240 |
| Composition 3 | 200 | 480 |

Each of these compositions was applied by spraying in a quantity of 1 l/ha to plants of *Chenopodium album* and *Galium aparine* in pots at the 3 to 4 leaf stage in the doses indicated in Table III.

The herbicidal effect of composition 1 on *Chenopodium album* and on *Galium aparine* and the herbicidal effects of compositions 2 and 3 on *Chenopodium album* alone were evaluated after 21 days.

The results of these tests are set out in Table III.

The "Expected results" end "Results obtained" are as defined in Example 1.

TABLE III

|  | Results obtained (%) after individual application of the constituents of the composition | | | | Expected results (%) for the | | | Results obtained (%) for the | | |
|---|---|---|---|---|---|---|---|---|---|---|
|  |  |  |  |  | 1 | 2 | 3 | 1 | 2 | 3 |
| Bromoxynil octanoate (g/ha) | 100 | 200 | 0 | 0 | 100 | 200 | 200 | 100 | 200 | 200 |
| Prosulfocarbe (g/ha) | 0 | 0 | 240 | 480 | 240 | 240 | 480 | 240 | 240 | 480 |
| Chenopodium album | 0 | 55 | 0 | 5 | 0 | 55 | 57 | 70 | 95 | 100 |
| Galium aparine | 40 | 75 | 10 | 13 | 46 | — | —* | 70 | — | — |

*indicates that the test was not carried out on the species or in the doses in question It can be seen from this Table that a synergistic effect is developed between the bromoxynil octanoate and the prosulfocarbe.

EXAMPLE 3

Composition based on ioxynil octanoate and diallate

Four phytosanitary compositions according to the invention were prepared in the form of emulsifiable concentrates of which the respective formulations are shown in Table IV.

TABLE IV

|  | Ioxynil octanoate (g/l) | Diallate (g/l) |
|---|---|---|
| Composition 1 | 192 | 200 |
| Composition 2 | 192 | 400 |
| Composition 3 | 96 | 400 |
| Composition 4 | 48 | 400 |

Each of these compositions was applied by spraying in a quantity of 0.5, 1, 1 and 2 l/ha, respectively, to plants of *Chenopodium album*, *Galium aparine* and *Matricaria inodora* in pots at the 3 to 4 leaf stage in the doses indicated in Table V.

The herbicidal select of each of the compositions on the treated species was evaluated after 21 days.

The results of these tests are set out in Table V.

The "Expected results" and "Results obtained" are as defined in Example 1.

TABLE V

|  | Results obtained (%) after individual application of the constituents of the composition | | | | | Expected results (%) for the compositions | | | | Results obtained (%) for the compositions | | | |
| --- | --- | --- | --- | --- | --- | --- | --- | --- | --- | --- | --- | --- | --- |
|  |  |  |  |  |  | 1 | 2 | 3 | 4 | 1 | 2 | 3 | 4 |
| Ioxynil octanoate (g/ha) | 96 | 0 | 0 | 0 | 0 | 96 | 96 | 96 | 96 | 96 | 96 | 96 | 96 |
| Diallate (g/ha) | 0 | 100 | 200 | 400 | 800 | 100 | 200 | 400 | 800 | 100 | 200 | 400 | 800 |
| Chenopodium album | 40 | 0 | 0 | 0 | 0 | 40 | 40 | 40 | 40 | 55 | 95 | 100 | 100 |
| Galium aparine | 60 | 5 | 10 | 5 | 5 | 62 | 64 | 62 | 62 | 85 | 80 | 85 | 93 |
| Matricaria inodora | 20 | 0 | 0 | 0 | 0 | 20 | 20 | 20 | 20 | 45 | 40 | 35 | 30 |

It can be seen from this Table that a synergistic effect is developed between the ioxynil octanoate and the diallate.

EXAMPLE 4

Composition based on bromoxynil octanoate and molinate

Four phytosanitary compositions according to the invention were prepared in the form of emulsifiable concentrates of which the respective formulations are shown in Table VI.

TABLE VI

|  | Bromoxynil octanoate (g/l) | Molinate (g/l) |
| --- | --- | --- |
| Composition 1 | 192 | 400 |
| Composition 2 | 96 | 400 |
| Composition 3 | 48 | 400 |
| Composition 4 | 48 | 800 |
| Composition 5 | 192 | 400 |
| Composition 6 | 96 | 400 |
| Composition 7 | 48 | 400 |

Compositions 1 to 4 were applied by spraying in quantities of 0.25, 0.5, 1 and 1 l/ha, respectively, to plants of Amaranthus sp. in pots and Compositions 2 to 7 were applied by spraying in quantities of 0.5, 1, 1, 0.5, 1 and 2 l/ha, respectively, to plants of Chenopodium album and on Galium aparine in pots at the 3 to 4 leaf stage in the doses indicated in Table VII.

The herbicidal effect of each of these compositions on the treated species was evaluated after 21 days.

The results of these tests are set out in Tables VII A and VII B.

The "Expected results" and "Results obtained" are as defined in Example 1.

TABLE VII A

|  | Results obtained (%) after individual application of the constituents of each composition | | | | | |
| --- | --- | --- | --- | --- | --- | --- |
| Bromoxynil octanoate (g/ha) | 48 | 96 | 0 | 0 | 0 | 0 |
| Molinate (g/ha) | 0 | 0 | 100 | 200 | 400 | 800 |
| Amaranthus sp. | 55 | — | 0 | 0 | 0 | 0 |
| Chenopodium album | 0 | 0 | — | 0 | 0 | 0 |
| Galium aparine | 25 | 30 | — | 0 | 0 | 0 |

TABLE VII B

|  | Expected results (%) for the compositions | | | | | | | Results obtained (%) for the compositions | | | | | | |
| --- | --- | --- | --- | --- | --- | --- | --- | --- | --- | --- | --- | --- | --- | --- |
|  | 1 | 2 | 3 | 4 | 5 | 6 | 7 | 1 | 2 | 3 | 4 | 5 | 6 | 7 |
| Bromoxynil ocatanoate (g/ha) | 48 | 48 | 48 | 48 | 96 | 96 | 96 | 48 | 48 | 48 | 48 | 96 | 96 | 96 |
| Molinate (g/ha) | 100 | 200 | 400 | 800 | 200 | 400 | 800 | 100 | 200 | 400 | 800 | 200 | 400 | 800 |
| Amaranthus sp. | 55 | 55 | 55 | 55 | — | — | — | 75 | 70 | 75 | 75 | — | — | — |
| Chenopodium album | — | 0 | 0 | 0 | 0 | 0 | 0 | — | 15 | 60 | 60 | 30 | 55 | 85 |
| Galium aparine | — | 25 | 25 | 25 | 30 | 30 | 30 | — | 35 | 83 | 90 | 50 | 50 | 70 |

It can be seen from this Table that a synergistic effect is developed between the bromoxynil octanoate and the molinate.

EXAMPLE 5

Composition based on bromoxynil octanoate and metolachlore

Three phytosanitary compositions according to the invention were prepared in the form of emulsifiable concentrates of which the respective formulations are shown in Table VIII.

TABLE VIII

|  | Bromoxynil octanoate (g/l) | Metolachlore (g/l) |
| --- | --- | --- |
| Composition 1 | 192 | 480 |
| Composition 2 | 96 | 480 |
| Composition 3 | 64 | 640 |

TABLE VIII-continued

|  | Bromoxynil octanoate (g/l) | Metolachlore (g/l) |
|---|---|---|
| Composition 4 | 32 | 640 |
| Composition 5 | 192 | 240 |

Compositions 1 and 2 were applied by spraying in quantities of 0.25 and 0.5 l/ha, respectively, to plants of *Galium aparine* in pots,
Compositions 3 and 4 were applied by spraying in quantities of 0.75 and 1.5 l/ha, respectively, to plants of *Solanum nigrum* and on *Matricaria inodora* in pots and
Compositions 3, 4 and 5 were applied by spraying in quantities of 0.75, 1.5 and 0.5 l/ha, respectivelly, to plants of *Chenopodium album* and *Veronica* sp. at the 3 to 4 leaf stage in the doses indicated in Table IX.

The herbicidal effect of each of these compositions on the treated species was evaluated after 21 days.

The results of these tests are set out in Tables IX A and IX B.

The "Expected results" and "Results obtained" are as defined in Example 1.

TABLE IX A

|  | Results obtained (%) after individual application of the constituents of each composition | | | | | |
|---|---|---|---|---|---|---|
| Bromoxynil octanoate (g/ha) | 48 | 96 | 0 | 0 | 0 | 0 |
| Metolachlore (g/ha) | 0 | 0 | 120 | 240 | 480 | 960 |
| *Galium aparine* | 25 | — | 0 | 5 | — | — |
| *Solanum nigrum* | 25 | — | — | — | 0 | 0 |
| *Chenopodium album* | 5 | 7 | 0 | — | 5 | 5 |
| *Matricaria inodora* | 5 | — | — | — | 5 | 5 |
| *Veronica* sp. | 20 | 25 | 7 | — | 7 | 15 |

TABLE IX B

|  | Expected results (%) for the compositions | | | | | Results obtained (%) for the compositions | | | | |
|---|---|---|---|---|---|---|---|---|---|---|
|  | 1 | 2 | 3 | 4 | 5 | 1 | 2 | 3 | 4 | 5 |
| Bromoxynil octonoate (g/ha) | 48 | 48 | 48 | 48 | 96 | 48 | 48 | 48 | 48 | 96 |
| Metolachlore (g/ha) | 120 | 240 | 480 | 960 | 120 | 120 | 240 | 480 | 960 | 120 |
| *Galium aprine* | 25 | 29 | — | — | — | 45 | 45 | — | — | — |
| *Solanum nigrum* | — | — | 25 | 25 | — | — | — | 40 | 50 | — |
| *Chenopodium album* | — | — | 10 | 10 | 7 | — | — | 95 | 100 | 97 |
| *Matricaria inodora* | — | — | 10 | 10 | — | — | — | 40 | 60 | — |
| *Veronica* sp. | — | — | 26 | 32 | 30 | — | — | 95 | 90 | 97 |

It can be seen from this Table that a synergistic effect is developed between the bromoxynil octanoate and the metolachlore.

EXAMPLE 6

Composition based on ioxynil octanoate and fluazifop-p-butyl

A phytosanitary composition according to the invention was prepared in the form of emulsifiable concentrate containing:

96 g/l ioxynil octanoate and
124 g/l of fluazifop-p-butyl
and was applied by spraying in a quantity of 0.5 l/ha to plants of *Galium aparine* and *Solanum nitrum* in pots at the 3 to 4 leaf stage in the doses indicated in Table X.

The herbicidal effect of this composition on the treated species was evaluated after 21 days.

The results of these tests are Set out in Table X.

The "Expected results" and "Results obtained" are as defined in Example 1.

TABLE X

|  | Results obtained (%) after individual application of the constituents of the composition | | Expected results (%) | Results obtained (%) |
|---|---|---|---|---|
| Ioxynil octanote (g/ha) | 48 | 0 | 48 | 48 |
| Fluazifop-p-butyl (g/ha) | 0 | 62 | 62 | 62 |
| *Galium aparine* | 20 | 5 | 24 | 45 |
| *Solanum nigrum* | 55 | 0 | 55 | 85 |

It can be seen from this Table that a synergistic effect is developed between the ioxynil octanoate and the fluazifop-p-butyl.

EXAMPLE 7

Composition based of bromoxynil octanoate and pirimiphos-methyl

Four phytosanitary compositions according to the invention were prepared in the form of emulsifiable concentrates of which the respective formulations are shown in Table XI.

TABLE XI

|  | Bromoxynil octanoate (g/l) | Pirimiphos-methyl (g/l) |
|---|---|---|
| Composition 1 | 360 | 75 |
| Composition 2 | 360 | 150 |
| Composition 3 | 320 | 267 |
| Composition 4 | 240 | 400 |

Each of these compositions was applied by spraying in quantities of 0.67, 0.67, 0.75 and 1 l/ha, respectively, to plants of *Stellaria media* and *Taraxacum officinale* in pots at the 3 to 4 leaf stage in the doses indicated in Table XII.

The herbicidal effect of each composition on the treated species was evaluated after 21 days.

The results of these tests are set out in Table XII.

The "Expected results" and "Results obtained" are as defined in Example 1.

TABLE XII

|  | Results obtained (%) after individual application of the constituents of the composition | | | | | Expected results (%) for the compositions | | | | Results obtained (%) for the compositions | | | |
|---|---|---|---|---|---|---|---|---|---|---|---|---|---|
|  |  |  |  |  |  | 1 | 2 | 3 | 4 | 1 | 2 | 3 | 4 |
| Bromoxynil octanoate (g/ha) | 240 | 0 | 0 | 0 | 0 | 240 | 240 | 240 | 240 | 240 | 240 | 240 | 240 |
| Pirimiphos-methyl (g/ha) | 0 | 50 | 100 | 200 | 400 | 50 | 100 | 200 | 400 | 50 | 100 | 200 | 400 |
| *Stellaria media* | 10 | 0 | 0 | 0 | 0 | 10 | 10 | 10 | 10 | 25 | 30 | 35 | 25 |
| *Taraxacim officinale* | 55 | 0 | 0 | 0 | 0 | 55 | 55 | 55 | 55 | 75 | 78 | 75 | 80 |

It can be seen from this Table that a synergistic effect is developed between the bromoxynil octanoate and the pirimiphos-methyl.

EXAMPLE 8

Composition based on ioxynil octanoate and fenpropimorphe

Eleven phytosanitary compositions according to the invention were prepared in the form of emulsifiable concentrates of which the respective formulations are shown in Table XIII.

TABLE XIII

|  | Ioxynil octanoate (g/l) | Fenpropimorphe (g/l) |
|---|---|---|
| Composition 1 | 150 | 470 |
| Composition 2 | 75 | 470 |
| Composition 3 | 40 | 500 |
| Composition 4 | 240 | 375 |
| Composition 5 | 120 | 375 |
| Composition 6 | 80 | 500 |
| Composition 7 | 48 | 600 |
| Composition 8 | 360 | 282 |
| Composition 9 | 240 | 375 |
| Composition 10 | 160 | 500 |
| Composition 11 | 96 | 600 | compositions 1, 2 and 3 were applied by spraying in quantities of 0.2, 0.4 and 0.75 l/ha, respectively, to plants of *Solanum nigrum* in pots,
compositions 1, 2, 8 and 10 were applied by spraying in quantities of 0.2, 0.4, 0.33 and 0.75 l/ha, respectively, to plants of *Galium aparine* in pots,
compositions 4, 5, 6 and 7 were applied by spraying in quantities of 0.25, 0.5, and 0.75 and 1.25 l/ha, respectively, to plants of *Chenopodium album* in pots,
compositions 4, 8, 9, 10 and 11 were applied by spraying in quantites of 0.25, 0.33, 0.5, 0.75 and 1.25 l/ha, respectively, to plants of *Matricaria inodora* in pots,
compositions 8, 9 and 10 were applied by spraying in quantities of 0.33, 0.5, and 0.75 l/ha, respectively, to plants of *Taraxacum officinale* in pots and compositions 8, 9, 10 and 11 were applied by spraying in quantites of 0.33, 0.5, 0.7 and 1.25 l/ha, respectively, to plants of *Daucus carota* in pots, at the 3 to 4 leaf stage in the doses indicated in Tables XIV A, XIV B and XIV C.

The herbicidal effect of each of the compositions on the treated species was evaluated after 21 days.

The results of these tests are set out in Tables XIV A, XIV B end XIV C.

The "Expected results" and "Results obtained" are as defined in Example 1.

TABLE XIV A

|  | Results obtained (%) after individual application of the constituents of each composition | | | | | | |
|---|---|---|---|---|---|---|---|
| Ioxynil octanoate (g/ha) | 30 | 60 | 120 | 0 | 0 | 0 | 0 |
| Fenpropimorphe (g/ha) | 0 | 0 | 0 | 94 | 187 | 375 | 750 |
| Solanum nigrum | 30 | — | — | 0 | 0 | 3 | — |
| Galium aparine | 20 | — | 35 | 3 | 3 | 10 | — |
| Chenopodium album | — | 0 | — | 0 | 0 | 3 | 5 |
| Matricaria inodora | — | 30 | 25 | 8 | 5 | 8 | 5 |
| Taraxacum officinale | — | — | 15 | 0 | 0 | 0 | — |
| Daucus carota | — | — | 50 | 0 | 0 | 3 | 5 |

TABLE XIV B

|  | Expected results (%) for the compositions | | | | | | | | | | |
|---|---|---|---|---|---|---|---|---|---|---|---|
|  | 1 | 2 | 3 | 4 | 5 | 6 | 7 | 8 | 9 | 10 | 11 |
| Ioxynil octanoate (g/ha) | 30 | 30 | 30 | 60 | 60 | 60 | 60 | 120 | 120 | 120 | 120 |
| Fenpropimorphe (g/ha) | 94 | 187 | 375 | 94 | 187 | 375 | 750 | 94 | 187 | 375 | 750 |
| Solanum nigrum | 30 | 30 | 32 | — | — | — | — | — | — | — | — |
| Galium aparine | 22 | 22 | — | — | — | — | — | 37 | — | 42 | — |
| Chenopodium album | — | — | — | 0 | 0 | 3 | 5 | — | — | — | — |
| Matricaria inodora | — | — | — | 36 | — | — | — | 31 | 29 | 31 | 29 |
| Taraxacum officinale | — | — | — | — | — | — | — | 15 | 15 | 15 | — |
| Daucus carota | — | — | — | — | — | — | — | 50 | 50 | 52 | 53 |

TABLE XIV C

|  | Results obtained (%) for the compositions | | | | | | | | | | |
|---|---|---|---|---|---|---|---|---|---|---|---|
|  | 1 | 2 | 3 | 4 | 5 | 6 | 7 | 8 | 9 | 10 | 11 |
| Ioxynil octanoate (g/ha) | 30 | 30 | 30 | 60 | 60 | 60 | 60 | 120 | 120 | 120 | 120 |
| Fenpropimorphe (g/ha) | 94 | 187 | 375 | 94 | 187 | 375 | 750 | 94 | 187 | 375 | 750 |
| Solanum nigrum | 45 | 40 | 65 | — | — | — | — | — | — | — | — |
| Galium aparine | 35 | 35 | — | — | — | — | — | 55 | — | 65 | — |
| Chenopodium album | — | — | — | 10 | 45 | 83 | 90 | — | — | — | — |
| Matricaria inodora | — | — | — | 55 | — | — | — | 70 | 70 | 80 | 85 |
| Taraxacum officinale | — | — | — | — | — | — | — | 40 | 35 | 55 | — |
| Daucus carota | — | — | — | — | — | — | — | 65 | 70 | 70 | 75 |

It can be seen from this Table that a synergistic effect is developed between the ioxynil octanoate and the fenpropimorphe.

EXAMPLE 9

Composition based on ioxynil octanoate and λ-cyhalothrin

Eight phytosanitary compositions according to the invention were prepared in the form of emulsifiable concentrates of which the respective formulations are shown in Table XV.

TABLE XV

|  | Ioxynil octanoate (g/l) | λ-cyhalothrin (g/l) |
|---|---|---|
| Composition 1 | 240 | 25 |
| Composition 2 | 240 | 50 |
| Composition 3 | 240 | 100 |
| Composition 4 | 120 | 100 |
| Composition 5 | 240 | 12.5 |
| Composition 6 | 240 | 25 |

TABLE XV-continued

|  | Ioxynil octanoate (g/l) | λ-cyhalothrin (g/l) |
|---|---|---|
| Composition 7 | 240 | 50 |
| Composition 8 | 240 | 100 |

Compositions 1 to 4 were applied by spraying in quantities of 0.25, 0.25, 0.25 and 0.5 l/ha, respectively, to plants of *Chenopodium album*, *Matricaria inodora* and *Solanum nigrum* in pots,
each composition 5 to 8 was applied by spraying in quantity of 0.5 l/ha to plants of *Galium aparine* in pots, and
each of compositions 7 and 8 was applied by spraying in a quantity of 0.5 l/ha to plants of *Taraxacum officinale* and *Veronica* sp. in pots at the 3 to 4 leaf stage in the doses indicated in Tables XVI A, XVI B and XVI C.

The herbicidal effect of each composition on the treated species was evaluated after 21 days.

The results of these tests are set out in Tables XVI A, XVI B and XVI C.

The "Expected results" end "Results obtained" are as defined in Example 1.

TABLE XVI A

|  | Results obtained (%) after individual application of the constituents of each composition | | | | | |
|---|---|---|---|---|---|---|
| Ioxynil octanoate (g/ha) | 60 | 120 | 0 | 0 | 0 | 0 |
| λ-cyhalothrin (g/ha) | 0 | 0 | 6.25 | 12.5 | 25 | 50 |
| *Chenopodium album* | 8 | — | 0 | 0 | 0 | 0 |
| *Matricaria inodora* | 20 | — | 0 | 0 | 0 | 0 |
| *Solanum nigrum* | 45 | — | 0 | 0 | 0 | 0 |
| *Galium aparine* | — | 25 | 0 | 0 | 0 | 0 |
| *Taraxacum officinale* | — | 25 | 0 | 0 | 0 | 0 |
| *Veronica* sp. | — | 55 | 0 | 0 | 0 | 0 |

TABLE XVI B

|  | Expected results (%) for the compositions | | | | | | | |
|---|---|---|---|---|---|---|---|---|
|  | 1 | 2 | 3 | 4 | 5 | 6 | 7 | 8 |
| Ioxynil octanoate (g/ha) | 60 | 60 | 60 | 60 | 120 | 120 | 120 | 120 |
| λ-Cyhalothrin (g/ha) | 6.25 | 12.5 | 25 | 50 | 6.25 | 12.5 | 25 | 50 |
| *Chenopodium album* | 8 | 8 | 8 | 8 | — | — | — | — |
| *Matricaria inodora* | 20 | 20 | 20 | 20 | — | — | — | — |
| *Solanum nigrum* | 45 | 45 | 45 | 45 | — | — | — | — |
| *Galium aparine* | — | — | — | — | 25 | 25 | 25 | 25 |
| *Taraxacum officinale* | — | — | — | — | — | — | 25 | 25 |
| *Veronica* sp. | — | — | — | — | — | — | 55 | 55 |

TABLE XVII B

|  | Results obtained (%) for the compositions | | | | | | | |
|---|---|---|---|---|---|---|---|---|
|  | 1 | 2 | 3 | 4 | 5 | 6 | 7 | 8 |
| Ioxynil octanoate (g/ha) | 60 | 60 | 60 | 60 | 120 | 120 | 120 | 120 |
| λ-Cyhalothrin | 6.25 | 12.5 | 25 | 50 | 6.25 | 12.5 | 25 | 50 |
| *Chenopodium album* | 18 | 20 | 25 | 50 | — | — | — | — |
| *Matricaria inodora* | 20 | 35 | 45 | 50 | — | — | — | — |
| *Solanum nigrum* | 60 | 70 | 75 | 85 | — | — | — | — |
| *Galium aparine* | — | — | — | — | 35 | 40 | 45 | 45 |
| *Taraxacum officinale* | — | — | — | — | — | — | 50 | 45 |
| *Veronica* sp. | — | — | — | — | — | — | 70 | 75 |

It can be seen from this Table that a synergistic effect is developed between the ioxynil octanoate and the λ-cynalothrin.

EXAMPLE 10

Composition based on ioxynil octanoate and sulfosate

Eighteen phytosanitary compositions according to the invention were prepared; seven of these compositions contained only one of the above two constituents and the nine other comprised the two constituents in the form of emulsifiable concentrates of which the respective formulations are shown in Table XVII.

TABLE XVII

|  | Ioxynil octanoate (g/hl) | Sulfosate (g/hl) |
|---|---|---|
| Composition 1 | 0 | 60 |
| Composition 2 | 0 | 120 |
| Composition 3 | 0 | 240 |
| Composition 4 | 0 | 480 |
| Composition 5 | 30 | 0 |
| Composition 6 | 30 | 60 |
| Composition 7 | 30 | 120 |
| Composition 8 | 30 | 240 |
| Composition 9 | 60 | 0 |
| Composition 10 | 60 | 60 |
| Composition 11 | 60 | 120 |
| Composition 12 | 60 | 240 |
| Composition 13 | 60 | 480 |
| Composition 14 | 120 | 0 |
| Composition 15 | 120 | 60 |
| Composition 16 | 120 | 120 |
| Composition 17 | 120 | 240 |
| Composition 18 | 120 | 480 |

The above-mentioned compositions were applied by spraying to plants in pots of the following group: Ambrosia, Brassica, Chenopodium, Daucus, Galium, Matricaria, Rumex, Solanum, Stellaria, Taraxacum.

The percentages destruction are observed after 22 days. These results are recorded in Table XVIIA.

TABLE XVII A

| Plants tested | Results (%) obtained with the compositions | | | | | | | | | | | | | | | | | |
|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 | 15 | 16 | 17 | 18 |
| Ambrosia | 25 | 30 | 65 | 75 | 25 | 35 | 40 | 45 | 45 | 55 | 90 | 90 | 95 | 65 | 100 | 85 | 85 | 90 |
| Brassica | 10 | 20 | 10 | 30 | 20 | 30 | 35 | 45 | 45 | 60 | 60 | 70 | 70 | 60 | 75 | 80 | 83 | 85 |
| Chenopodium | 0 | 20 | 60 | 90 | 75 | 70 | 50 | 60 | 60 | 60 | 60 | 80 | 95 | 65 | 75 | 80 | 90 | 90 |
| Daucus | 5 | 0 | 20 | 78 | 20 | 70 | 83 | 83 | 45 | 80 | 95 | 95 | 200 | 70 | 100 | 100 | 100 | 100 |
| Galium | 8 | 10 | 20 | 50 | 20 | 35 | 35 | 50 | 45 | 55 | 60 | 65 | 83 | 55 | 80 | 80 | 80 | 85 |

TABLE XVII A-continued

| Plants tested | Results (%) obtained with the compositions | | | | | | | | | | | | | | | | | |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 |
| Matricaria | 30 | 35 | 65 | 93 | 25 | 95 | 80 | 98 | 70 | 80 | 95 | 95 | 98 | 70 | 95 | 100 | 100 | 100 |
| Rumex | 55 | 50 | 60 | 80 | 35 | 45 | 55 | 65 | 50 | 70 | 75 | 85 | 90 | 70 | 65 | 80 | 85 | 93 |
| Solanum | 20 | 25 | 60 | 65 | 40 | 40 | 60 | 60 | 78 | 75 | 80 | 70 | 95 | 70 | 95 | 80 | 95 | 85 |
| Stellaria | 35 | 55 | 70 | 93 | 13 | 55 | 85 | 65 | 20 | 83 | 88 | 90 | 98 | 60 | 55 | 80 | 85 | 95 |
| Taraxacum | 60 | 60 | 70 | 85 | 20 | 45 | 50 | 60 | 45 | 88 | 85 | 98 | 100 | 55 | 100 | 95 | 98 | 100 |
| Average | 25 | 31 | 50 | 74 | 29 | 52 | 57 | 63 | 50 | 71 | 79 | 84 | 92 | 64 | 84 | 86 | 90 | 92 |

The excellent properties of the compositions according to the invention result from the examination of this Table.

With respect to two of the above-mentioned plants, i.e. *Daucus carota* and *Matricaria inodora*, the "Expected results" (defined in example 1) and "Results obtained" were compared; the recorded results are collected in Table XVII B.

TABLE XVII B

| Plants tested | | Compositions applied | | | | | | | | |
|---|---|---|---|---|---|---|---|---|---|---|
| | | 6 | 7 | 8 | 10 | 11 | 12 | 15 | 16 | 17 |
| Daucus carota | "Expected results" (%) | 25 | 20 | 36 | 48 | 43 | 56 | — | — | — |
| | "Results obtained" (%) | 70 | 83 | 83 | 80 | 95 | 95 | — | — | — |
| Matricaria inodora | "Expected results" (%) | 48 | 51 | 73 | — | — | — | 79 | 81 | 89 |
| | "Results obtained" (%) | 95 | 80 | 98 | — | — | — | 95 | 100 | 100 |

The examination of the results collected in this Table shows that it exists an important synergistic effect for *Daucus carota* and *Matricaria inodora*. The better synergistic effects are obtained with low doses of the two products.

We claim:

1. A liquid phytosanitary composition to be applied by spraying onto plants consisting essentially of a diluent and of a solution of a liquid active composition, said liquid active composition consisting essentially of an oxynil and at least one active substance liquid at ambient temperature capable of dissolving and maintaining therein the oxynil in the liquid state after application on said plants, the said substance being selected from the group consisting of herbicides, the said herbicides being selected from the group consisting of S-alkyl-thiolcarbamates, chloracetanilides, butamifos, cinmethylin, clethodim, isopropalin, clomazone, dalapon, tebutame, sulfosate, methyl (R)-2-[7-(2-chloro-α,α,α-trifluoro-p-tolyloxy)-2-naphthyloxy] propionate and (+)-tetrahydrofurfuryle (R) -2-[4-(6-chloro-quinoxaline-2-yloxy ) phenoxy] propanoate.

2. A liquid phytosanitary composition according to claim 1, containing 48 to 450 grams oxynil per liter.

3. A liquid phytosanitary composition according to one of claims 1 and 2, wherein the S-alkyl-thiolcarbamate is selected from the group consisting of EPTC, pebulate, cycloate, butylate, vernolate, diallate, triallate and molinate.

4. A liquid phytosanitary composition according to one of claims 1 and 2, wherein the chloracetanilide is selected from the group consisting of acetochlore, butachlore, butenachlore, metolachlore and pretilachlore.

5. A process for applying a herbicidal treatment to a plant, comprising spraying on the plant to be treated a quantity sufficient to supply 48 to 450 grams oxynil per hectare of the treated plants, of a liquid phytosanitary active composition consisting essentially of a diluent and of a solution of a liquid active composition, said liquid active composition consisting essentially of an oxynil and at least one substance liquid at ambient temperature capable of dissolving and maintaining therein the oxynil in the liquid state after application on said plants, the said substance being selected from the group consisting of herbicides, the said herbicides being selected from the group comprising S-alkyl-thiolcarbamates, chloracetanilides, butamifos, cinmethylin, clethodim, isopropalin, clomazone, dalapon, tebutame, sulfosate, methyl (R)-2-[7-(2-chloro-α,α,α-tri-fluoro-p-tolyloxy)-2-naphthyloxy] propionate and (+)-tetrahydrofurfuryle (R)-2-[4-(6-chloro-quinoxaline-2-yloxy) phenoxy] propanoate.

* * * * *